(12) United States Patent
Cynshi et al.

(10) Patent No.: US 7,803,779 B2
(45) Date of Patent: Sep. 28, 2010

(54) DRUGS FOR THE TREATMENT AND/OR PROPHYLAXIS OF GASTROPARESIS SYMPTOM

(75) Inventors: Osamu Cynshi, Gotenba (JP); Hisanori Takanashi, Tokyo (JP); Tatsuhiko Iwase, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 228 days.

(21) Appl. No.: 11/813,026

(22) PCT Filed: Dec. 28, 2005

(86) PCT No.: PCT/JP2005/024263
§ 371 (c)(1),
(2), (4) Date: Jun. 28, 2007

(87) PCT Pub. No.: WO2006/070937
PCT Pub. Date: Jul. 6, 2006

(65) Prior Publication Data
US 2009/0062219 A1    Mar. 5, 2009

(51) Int. Cl.
*A61K 31/70* (2006.01)
(52) U.S. Cl. ........................................................ 514/29
(58) Field of Classification Search .................. 536/7.2; 514/29
See application file for complete search history.

(56) References Cited

U.S. PATENT DOCUMENTS 5,658,888 A * 8/1997 Koga et al. ..................... 514/29

FOREIGN PATENT DOCUMENTS

| EP | 0 643 068 B1 | 8/1998 |
|---|---|---|
| WO | WO 01/60833 A2 | 8/2001 |
| WO | WO 2004/037273 A1 | 5/2004 |

OTHER PUBLICATIONS

J. Arts et al., "Influence of erythromycin on gastric emptying and meal related symptoms in functional dyspepsia with delayed gastric emptying", *Gut*, vol. 54, pp. 455-460, 2005, downloaded from gut.bmj.com on Oct. 9, 2007.
J. J. Galligan et al., "Basic and clinical pharmacology of new motility promoting agents", *Neurogastroenterol Motil*, vol. 17, pp. 643-653, 2005.
N. J. Talley et al., "Failure of a motilin receptor agonist (ABT-229) to relieve the symptoms of functional dyspepsia in patients with and without delayed gastric emptying: a randomized double-blind placebo-controlled trial", *Aliment Pharmacol Ther*. vol. 14, pp. 1653-1661, 2000.
A. Sturm et al., "Prokinetics in Patients with Gastroparesis: A Systematic Analysis", *Digestion*, vol. 60, pp. 422-427, 1999.
R. Dhir et al., "Erythromycin in the Short- and Long-term Control of Dyspepsia Symptoms in Patients with Gastroparesis", *Clin. Gastroenterol*, vol. 38, No. 3, pp. 237-242, Mar. 2004.
K. Maganti et al., "Oral Erythromycin and Symptomatic Relief of Gastroparesis: A Systematic Review", *American journal of Gastroenterology*, vol. 98, No. 2, 2003.
D. Scott Smith et al., "Current Conepts in Diabetic Gastroparesis", *Drugs*, vol. 63, No. 13, pp. 1339-1358, 2003.
D. O'Donovan et al., "Idiopathic and Diabetic Gastroparesis", *Current Treatment Options in Gastroenterology*, vol. 6, pp. 299-309, 2003.
R. M. McCallum et al., "Gastric Dysmotility and Gastroparesis", *Current Treatment Options in Gastroenterology*, vol. 4, pp. 179-191, 2001.
M. Kipnes et al., "Safety of Mitemcinal Fumarate (GM-611) in Patients with Symptomatic Gastroparesis", *Clinical Therapeutics/New Technology-Pharmacologic Treatment of Diabetic Complications*, 558-P, XP009063405.
Chugai Pharmaceutical Co., Ltd., Development Pipeline, pp. 15-17, Jun. 2003.
Chugai Prma USA., "Safety and Effectiveness of an Investigational Agent (GM-611) in patients with Diabetic Gastroparesis", *ClinicalTrials.Gov*, downloaded http://web.org/web/20077023740/http://clinicaltrials.gov/ct/show/N... Oct. 17, 2007.

(Continued)

*Primary Examiner* — Elli Peselev
(74) *Attorney, Agent, or Firm* — Browdy and Neimark, PLLC (57) ABSTRACT

The present invention provides a therapeutic and/or preventive agent against gastroparesis symptom which is appropriate for continuous medication and which comprises a compound represented by formula (1):

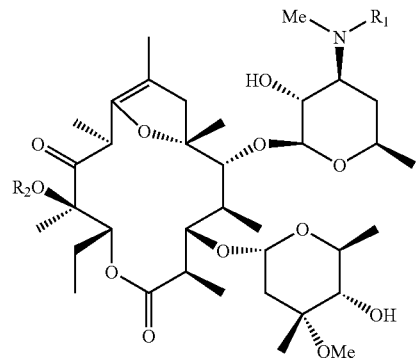

(wherein $R_1$ represents a $C_1$-$C_6$ alkyl group and $R_2$ represents a $C_1$-$C_6$ alkyl group) or a pharmaceutically acceptable salt thereof as an active ingredient. The erythromycin derivative of the formula (1) has an efficacy of improving gastroparesis and this action of the derivative in improving gastroparesis symptom is not found in ABT-229, a different motilin agonist erythromycin derivative. Further, the compound of the formula (1) is also appropriate for long-term clinical use because of its much weaker antibacterial action than that of erythromycin. Accordingly, the present invention provides a pharmaceutical agent that is safe and exhibits potent therapeutic and/or preventive effect in an effort to improve symptomatic gastroparesis.

3 Claims, 4 Drawing Sheets

OTHER PUBLICATIONS

H. Koga et al., "Design, SAR and pharmacology of GM-61, the first acid-stable nonpeptide motilin receptor agonist", *Drugs of the Future*, vol. 27, No. 3, pp. 255-272, 2002.

Program of the Annual Meeting of the American Gastroenterological Asociation and Digestive Disease Week, "Motilin-receptor agonist, accelerates gastric emptying in patients with symptomatic gastroparesis (GP)", May 20, 2001, Atlanta, Georgia. XP009063334.

AGA Abstracts, "Effcts of mitemcinal fumarate (GM-611) on gastric emptying in patients with idiopathic or diabetic gastroparesis", XP009063502.

WPI Derwent, "Agent for Treating and Preventing dyschezia comprises an erythromycin derivative", XP-002372362.

J. D. Faichney et al., Safety and Efficacy of Mitemcinal Fumarate (GM-611) in Diabetic Gastroparesis: 12-week, Multi-Center, Double-Blind, Placebo-Controlled, Phase 2b Study (GM-611-05), *Clinical Therapeutics/New Technology-Pharmacologic Treatment of Diabetic Complications*, 2126-PO, XP009063406.

S. Cucciara eet al., "Gastric Emptying Delay and Gastric Electrical Derangement in IDDM", Pathophysiology/Complications, *Diabetes Care*, vol. 21, No. 3, Mar. 1998.

C. E. M. DeBlock et al., "Delayed Gastric Emptying and Gastric Autoimmunity in Type 1 Diabetes", *Diabetes Care*, vol. 25, No. 5, pp. 912-917, May 2002.

J. Fang et al., "GM-611, A Motilin-Receptor Agonist, Accelerates Gastric Emptying in Patients with Symptomatic Gastroparesis"(GP), *CBI*, Apr. 2001.

J. Janssens et al., "Improvement of gastric Emptying in Diabetic Gastroparsis by Erythromycin", *New England Journal of Medicine*, pp. 1028-1031, Apr. 12, 1990.

H. Koga et al., "Potent, Acid-Stable and Orally Active Macrolide-Type Motilin Receptor Agonists, GM-611 and the Derivatives", *Bioorganic @ Medicinal Chemistry Letters*, vol. 4, No. 11, pp. 1347-1352, 1994.

Marie-France Kong et al., "Natural History of Diabetic Gastroparesis", *Diabetes Care*, vol. 22, No. 3, pp. 503-507, Mar. 1999.

A. Russo et al., "Effect of the motilin agonist KC 11458 on gastric emptying in diabetic gastoparesis", *Aliment Pharmacol. Ther.*, vol. 20, pp. 333-338, 2004.

N. J. Talley et al., "Diabetic Gastropathy and Prokinetics", *American Journal of Gastroenterology*, vol. 98, No 2, pp. 264-271, 2003.

N. J. Talley et al., "Effects of a motilin receptor agonist (ABT-229) on upper gastrointestinal symptoms in type 1 diabetes mellitus: a randomized, double-blind, placebo controlled trial", *Gut*, vol. 29, pp. 395-401, 2001. Downloaded from gutbmj.com on Oct. 9, 2007.

* cited by examiner

DRUGS FOR THE TREATMENT AND/OR PROPHYLAXIS OF GASTROPARESIS SYMPTOM

TECHNICAL FIELD

This invention relates to a therapeutic and/or preventive agent for gastroparesis symptom which comprises an erythromycin derivative as an active ingredient, as well as a method for treating and/or preventing gastroparesis symptom which comprises administering an effective dose of the therapeutic and/or preventive agent to patients, a drug to be used for the treatment and/or prophylaxis, the use of the erythromycin derivative in the manufacture of the drug, as well as a kit containing the erythromycin derivative and an instruction manual for administering a pharmaceutical composition containing the erythromycin derivative as an active ingredient.

BACKGROUND ART

Erythromycin and its derivatives are known to have motilin agonistic actions, among which accelerating gastric emptying is considered as a typical action (Janssens, Peeters et al. 1990). Gastroparesis is a symptom in the digestive tract that manifests itself in association with diabetes mellitus and the like; conventionally, it is considered a symptom that occurs from delayed gastric emptying and in Japan, the identification of delayed gastric emptying is employed to make definitive diagnosis of gastroparesis.

An idea of treating patients with delayed gastric emptying by accelerating gastric emptying using motilin agonists was put forth and the drugs were shown to accelerate gastric emptying in clinical settings (Maganti, Onyemere et al. 2003; Russo, Stevens et al 2004). It was shown that such delay of gastric emptying correlated with the motility of the digestive tract evaluated on an electrogastrogram (Cucchiara, Franzese et al. 1998). However, since the primary objective of treating gastroparesis is to improve gastroparesis symptom in the epigastrium, restoring gastric emptying is not the final goal of the treatment. In addition, it turned out that the delaying of gastric emptying did not commonly correlate with gastroparesis symptom (De Block, De Leeuw et al. 2002) and that many of the patients who presented with gastroparesis symptom did not show delayed gastric emptying (Kong, Horowitz et al. 1999), making it no longer rationale to adopt the strategy of achieving a symptomatic improvement through the acceleration of gastric emptying. Improving the gastroparesis symptom in patients having symptomatic gastroparesis is currently considered the most important objective in therapy and there is a need to provide therapeutic drugs that can improve the gastroparesis symptom in the patients.

Further, in a study of 383 patients with gastroparesis using the erythromycin derivative ABT-229 which had been shown clinically to be capable of accelerating gastric emptying, no efficacy in the patients with both delayed gastric emptying and non-delayed gastric emptying was reported, showing that accelerating gastric emptying was not relevant with the improvement in gastroparesis symptom (Talley, Verlinden et al. 2001). For ABT-229, a discovery may be found in J. Med. Chem. 2004, Vol. 47, pp. 1704-1708.

ABT-299

Under these situations, it is required in the treatment of gastroparesis to develop pharmaceuticals that not only accelerate the motility of the gastrointestinal tract such as gastric emptying but also improve the gastroparesis symptom. As of today, no drugs have ever been succeeded for the development that were demonstrated to improve gastroparesis symptom (Talley 2003) and the patients having gastroparesis are in need of therapeutic and/or preventive drugs for improving the gastroparesis symptom that enable them to perceive an improvement in the symptom and which can be administered over an extended period of time with sustained improvement in the symptom.

Speaking now of JP 6-56843 A and WO93/24509, these references mention that specific compounds of erythromycin derivatives have motilin-agonistic actions as well as the ability to enhance the motility of the upper digestive tract. Moreover, 8,9-didehydro-N-demethyl-9-deoxo-6,11-dideoxy-6, 9-epoxy-12-O-methyl-N-(1-methylethyl)-11-oxoerythromycin which is one of those typical compounds has been reported to have a much weaker antibacterial action than erythromycin, suggesting the potential of its long-term clinical use (Koga, Sato et al. 1994). Further, those compounds have been shown to accelerate gastric emptying in a clinical study (Fang, McCallum et al. 2001). However, it is not known whether those compounds, unlike the aforementioned erythromycin derivative ABT-229, are capable of improving gastroparesis symptom. Hence, as already mentioned above, there is a need to provide therapeutic and/or preventive agents against gastroparesis symptom that is capable for continuous medication.

DISCLOSURE OF THE INVENTION

As a result of the extensive and intensive studies made to overcome the problems stated above, the inventors of the present invention have found that specific kinds of erythromycin derivatives are suitable for continuous medication, can improve the symptom in the upper digestive tract and are appropriately used as therapeutic and/or preventive agents against gastroparesis symptom. The inventors have also found that the compounds of the present invention are of a different type than the erythromycin derivative ABT229 which accelerated gastric emptying in clinical settings but did not improve gastroparesis symptom. In other words, the inventors have found that the erythromycin derivatives of the present invention, without delayed gastric emptying or not, can improve gastroparesis symptom itself and, hence, gastric dyspepsia per se which is caused by such symptom.

Thus, the present invention relates to a therapeutic and/or preventive agent against gastroparesis symptom which comprises as an active ingredient a compound of formula (1) or a pharmaceutically acceptable salt thereof:

(wherein $R_1$ represents a $C_1$-$C_6$ alkyl group and $R_2$ represents a $C_1$-$C_6$ alkyl group).

The present invention also relates to a method for treating and/or preventing gastroparesis symptom in a patient having disease in the gastrointestinal tract, which comprises administering to the patient a therapeutic and/or preventive agent against gastroparesis symptom comprising a compound of the above formula (1) or a pharmaceutically acceptable salt thereof as an active ingredient in a sufficient dose to treat and/or prevent the gastroparesis symptom in the patient.

The present invention further relates to the use of a compound of formula (1) or a pharmaceutically acceptable salt thereof in the manufacture of drugs to be used for the treatment and/or prevention.

The present invention additionally relates to a kit containing a compound of the formula (1) or a pharmaceutically acceptable salt and an instruction manual for administering a pharmaceutical composition containing the compound or its pharmaceutically acceptable salt as an active ingredient.

BEST MODE FOR CARRYING OUT THE INVENTION

In a preferred embodiment as regards the compound of the formula (1) used as an active ingredient in the present invention, $R_1$ in the formula (1) is an isopropyl group. In a more preferred embodiment, $R_2$ in the formula (1) is a methyl group.

The disease to be treated and/or prevented by the present invention is symptomatic gastroparesis and it is, in a preferred embodiment, symptomatic gastroparesis not involving delayed gastric emptying and, in a more preferred embodiment, it is symptomatic gastroparesis in diabetes mellitus.

The present invention will be further described in greater detail.

In the compound of the formula (1) used as an active ingredient in the present invention, $R_1$ and $R_2$ each independently represent a $C_1$-$C_6$ alkyl group. As used herein, the $C_1$-$C_6$ alkyl group refers to a linear or branched alkyl group containing 1 to 6 carbon atoms. Specific examples include a methyl group, an ethyl group, an n-propyl group, an isopropyl group, an n-butyl group, an isobutyl group, a sec-butyl group, a tert-butyl group, a pentyl group, a neopentyl group, a hexyl group, etc. Preferred among these are linear or branched alkyl groups with 1 to 3 carbon atoms, such as a methyl group, an ethyl group, an n-propyl group, an isopropyl group, etc. A particularly preferred example of $R_1$ is an isopropyl group, and a particularly preferred example of $R_2$ is a methyl group.

The compound of the formula (1) may form a salt. Exemplary salts that can be formed include salts with inorganic acids such as hydrochloric acid, hydrobromic acid, hydroiodic acid and sulfuric acid, as well as with organic acids such as acetic acid, oxalic acid, maleic acid, fumaric acid, methanesulfonic acid, with a fumarate being preferred. The compound of the formula (1) or salts thereof may in turn form hydrates.

A preferred compound of the formula (1) is one where $R_1$ is an isopropyl group and $R_2$ is a methyl group, namely, 8,9-didehydro-N-demethyl-9-deoxo-6,11-dideoxy-6,9-epoxy-12-O-methyl-N-(1-methylethyl)-11-oxoerythromycin. More preferred is a fumarate of this compound, namely, 8,9-didehydro-N-demethyl-9-deoxo-6,11-dideoxy-6,9-epoxy-12-O-methyl-N-(1-methylethyl)-11-oxoerythromycin,(2E)-2-butenedioate [hereunder designated as GM-611].

The compound of the formula (1) used in the present invention is known and can be synthesized as described in, e.g. Bioorg & Med Chem Lett, Vol. 4, No. 11, page 1347, 1994; JP 6-56843 A (WO93/24509); JP 9-100291 A (WO97/06177); WO02/18403 or WO02/30943.

The disease to be treated and/or prevented by the present invention is symptomatic gastroparesis. Symptomatic gastroparesis is a condition of the upper digestive tract which, irrespective of its etiology, causes the patient to have a similar type of unidentified complaint to gastroparesis. Among the patients with symptomatic gastroparesis are included patients with a normal level of gastric emptying and patients suffering diabetes mellitus.

As used herein, the term "therapeutic and/or preventive agent" refers to a drug used for either treatment or prevention or for both treatment and prevention purposes. More specifically, this term refers to a drug used for treating and/or preventing the disease of interest mentioned above or inhibiting the disease from progressing to more advanced stages, thereby preventing further deterioration and/or keeping it in the present state.

The therapeutic and/or preventive agent against symptomatic gastroparesis according to the present invention preferably enables the patient to perceive an improvement in the symptom and can also be administered over an extended period of time with sustained improvement in the symptom. The patient can be considered to "perceive an improvement in the symptom" if the patient, when interviewed, answers that "there was an adequate relief in the overall evaluation of gastroparesis symptom as compared with the time before the therapy started."

The pharmaceutical composition of the present invention may be prepared in various dosage forms by mixing the compound of the formula (1) as an active ingredient with a physiologically acceptable solid or liquid pharmaceutical carrier as appropriate for the intended route of administration. Possible routes of administration include oral administration, parenteral administration (e.g., intravenous injection), sustained release-administration using sustained-release preparations, and local administration using local delivery catheters or the like. Pharmaceutical carriers include commonly used excipients, binders, disintegrating agents, lubricants, coating agents, solubilizers, emulsifiers, suspending agents, stabilizers, fats/oils, and solvents. Dosage forms include tablets, granules, pills, capsules, solutions, syrups, suspensions, emulsions, and injections.

Although the dose of a compound of the formula (1) according to the present invention may be chosen as appropriate for the age of a patient, the type of the disease to be treated and/or prevented, the severity of symptom, the intended route of administration and so on, the daily dose for adults may be from 0.1 to 200 mg, preferably from 1 to 100 mg. More specifically, when administered with a particularly preferred compound GM-611, an adult patient preferably receives 2 mg to 60 mg of the compound, which may be given in a single or divided doses.

EXAMPLES

The present invention will be further described in more detail by reference to the following examples which are by no means intended to limit the scope of the invention.

In the following examples, GM-611 (8,9-didehydro-N-demethyl-9-deoxo-6,11-dideoxy-6,9-epoxy-12-O-methyl-N-(1-methylethyl)-11-oxoerythromycin,(2E)-2-butenedioate) was used as a compound of the formula (1). This compound was synthesized in the laboratories of Chugai Pharmaceutical Co., Ltd. as described in WO02/18403 and WO02/30943. To evaluate the efficacy of GM-611 in improving subjective gastroparesis symptom, diabetic patients on insulin therapy were selected. Since the analyses in the following examples were after the key-open of clinical trial, $P<0.01$ in a two-tail test was considered to show a significant effect and $P<0.1$ a tendency.

Example 1

Effect of GM-611 on Gastroparesis Symptom in Diabetic Patients with a Normal Level of Gastric Emptying In order to assess the efficacy of GM-611 in improving subjective gastroparesis symptom, diabetic patients who were presenting with gastroparesis symptom despite a normal level of gastric emptying were selected. The reason for the selection of patients with a normal level of gastric emptying is as follows: the compound of the present invention has a gastric emptying accelerating action and an improvement in delayed gastric emptying might contribute to an improvement in the symptom, making it impossible to determine whether the compound was a direct agent for improving the symptom; patients with a normal level of gastric emptying were selected in order to avoid this artifact. At the doses indicated in FIG. 1, the compound of the present invention was administered twice daily at meals for 3 months in order to assess its efficacy. The placebo was GM-611-free tablets. All assessment in the subjective gastroparesis symptom was evaluated by an electric diary by phone. Starting one week after the initiation of medication, the patients were interviewed every week and asked whether in the past 7 days, you have had adequate relief of your gastroparesis symptoms, and the yes/no answers were recorded. Patients who had an adequate relief at a frequency of at least 50% of weekly evaluations for one month of medication were evaluated as "monthly responders". Patients who were evaluated as monthly responder for three consecutive months. were assigned as "complete responders" (CR).

[Results]

Figure 1:
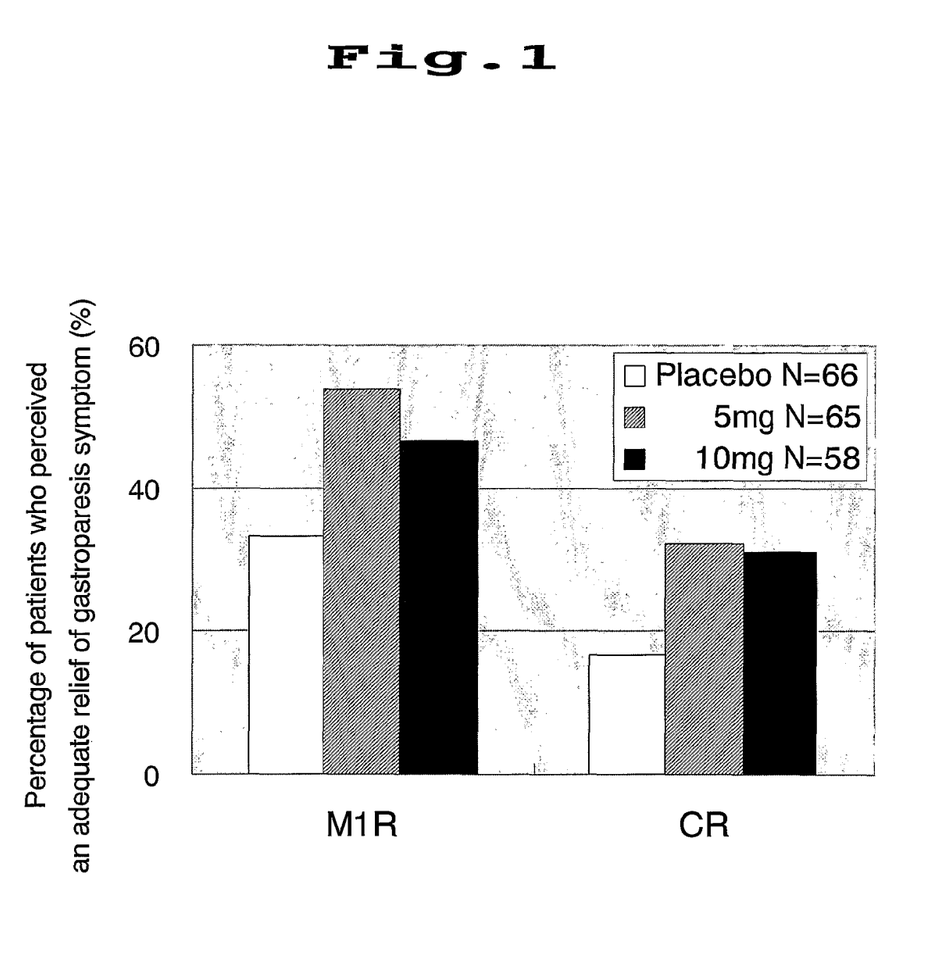
FIG. 1, which is titled "Effect of GM-611 on gastroparesis symptom in diabetic patients with a normal level of gastric emptying", is a graph showing results of evaluating the percentage of responders who were in the patients the gastroparesis symptom regardless a normal level of gastric emptying and who perceived an adequate relief of gastroparesis symptom by the administration of the therapeutic and/or preventive agent against gastroparesis symptom according to the present invention; M1R (month 1 responder) refers to patients who had adequate relief in at least 50% of weekly evaluations for the first one month of medication and CR (complete responder) refers to patients who were evaluated as monthly responder for three consecutive months.

The results are shown in FIG. 1. In neither of the GM-611 administered groups was recognized a significant inhibitory effect; however, in both of the GM-611 groups, the percentage of responders who had adequate relief in gastroparesis symptom were greater than those in the placebo group ($P=0.025$; CR rate in whole GM-611 treated group vs. placebo group by chi-square test). In addition, the efficacy of GM-611 had no apparent dose dependency.

The present inventors assumed that only the tendency toward improvement was recognized because the patients, who were too heterogenous in their pathological state, had such large individual variation that the drug efficacy was difficult to demonstrate. Hence, in order to obtain more definite results about the presence or absence of the drug efficacy, the inventors conducted additional analyses in patients who were more homogenous in their pathological state. To this end, three methods were used, one by selecting the patients with diabetes to type 1, another by selecting the patients to cases of good glycemic control, and the third by selecting the patients to cases having a longer history of diabetes. The results of the analyses in those homogenous sub-groups are described in the following Examples 2, 3 and 4.

Example 2

Effect of GM-611 on Gastroparesis Symptom in Patients of Type 1 Diabetes with a Normal Level of Gastric Emptying Since patients with type 2 diabetes receive a variety of treatments depending on the severity of the disease and are considered to present with diverse pathological states, only type 1 patients were subjected to the assessment of the efficacy of GM-611 in improving subjective gastroparesis symptom. The placebo was GM-611-free tablets.

[Results]

Figure 2:
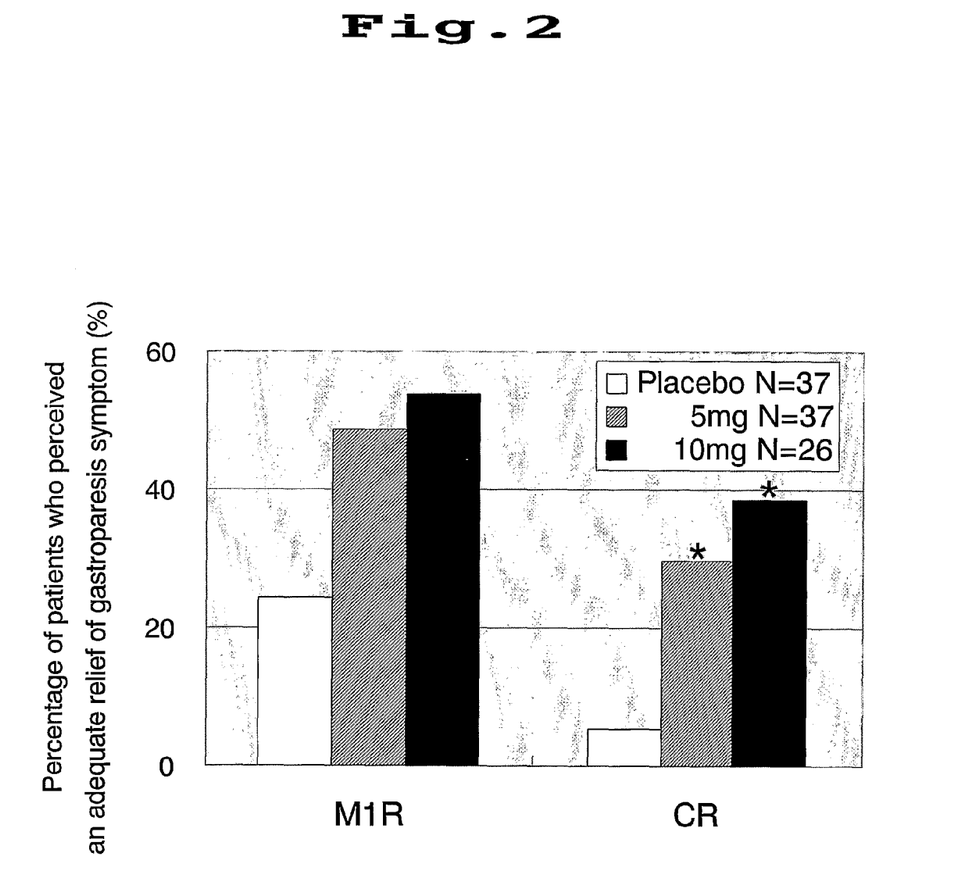
FIG. 2, which is titled "Effect of GM-611 on gastroparesis symptom in patients of type 1 diabetes with a normal level of gastric emptying", is a graph showing results of evaluating the percentage of responders who were in the patients of type 1 diabetes with the gastroparesis symptom regardless a normal level of gastric emptying and who perceived an adequate relief of gastroparesis symptom by the administration of the therapeutic and/or preventive agent against gastroparesis symptom according to the present invention; M1R (month 1 responder) refers to patients who had adequate relief in at least 50% of weekly evaluations for the first one month of medication and CR (complete responder) refers to patients who were evaluated as monthly responder for three consecutive months.

The results are shown in FIG. 2. As can be seen from the figure, the efficacy of GM-611 in improving the symptom was so marked as compared with the data shown in FIG. 1 that it can be described as significant ($P=0.001$; CR rate in whole GM-611 treated group vs. placebo group by chi-square test). The efficacy of GM-611 was dose-dependent. The fact that GM-611 apparently showed a significant improvement in gastroparesis symptom in a dose-dependent manner in the plausibly more homogenous patient groups was considered to show that the compound of the present invention can improve subjective gastroparesis symptom.

Example 3

Effect of GM-611 on Gastroparesis Symptom in Diabetic Patients of Good Glycemic Control with a Normal Level of Gastric Emptying Since symptoms in the gastrointestinal tract are considered to depend on whether blood glucose level is properly controlled, only diabetic patients with good glycemic control whose values of hemoglobin $A_{1C}$ (an index for the success of blood glucose control) were no more than 8% were subjected to the assessment of the efficacy of GM-611 in improving subjective gastroparesis symptom. The placebo was GM-611-free tablets.

[Results]

Figure 3:
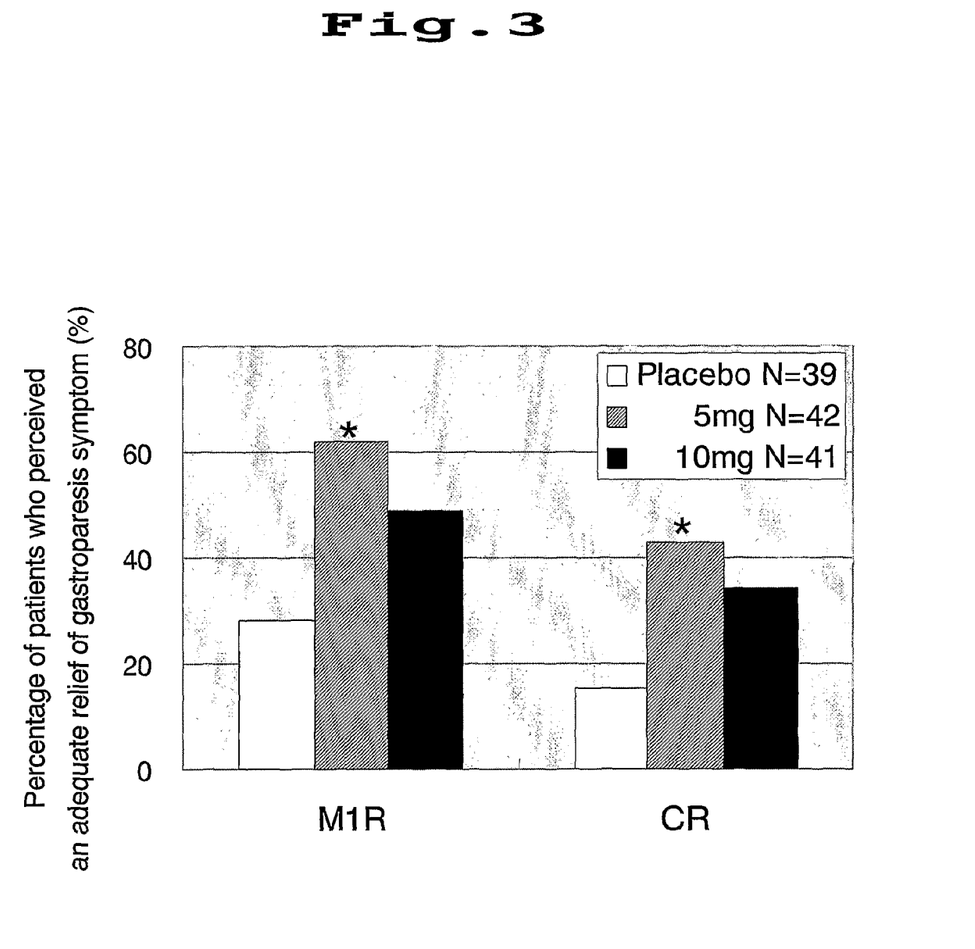
FIG. 3, which is titled "Effect of GM-611 on gastroparesis symptom in diabetic patients of good glycemic control with a normal level of gastric emptying", is a graph showing results of evaluating the percentage of responders who were in the diabetic patients with good glycemic control with the gastroparesis symptom regardless a normal level of gastric emptying and who perceived an adequate relief of gastroparesis symptom by the administration of the therapeutic and/or preventive agent against gastroparesis symptom according to the present invention; M1R (month 1 responder) refers to patients who had adequate relief in at least 50% of weekly evaluations for the first one month of medication and CR (complete responder) refers to patients who were evaluated as monthly responder for three consecutive months.

The results are shown in FIG. 3. Obviously, GM-611 showed a significant efficacy in improving the symptom ($P=0.010$; CR rate in whole GM-611 treated group vs. placebo group by chi-square test). The fact that GM-611 apparently showed a significant improvement in gastroparesis symptom in a dose-dependent manner in the plausibly more homogenous patient groups was considered to show that the compound of the present invention can improve subjective gastroparesis symptom.

Example 4

Effect of GM-611 on Gastroparesis Symptom in Diabetic Patients of Diabetic History Longer than 10 Years with a Normal Level of Gastric Emptying Since the early stage of diabetic development is considered to involve large variation in pathological state, particularly, in symptoms in the gastrointestinal tract, only diabetic patients with a longer-than-ten-year history from the onset of the diabetes were subjected to the assessment of the efficacy of GM-611 in improving subjective gastroparesis symptom. The placebo was GM-611 free tablets.

[Results]

Figure 4:
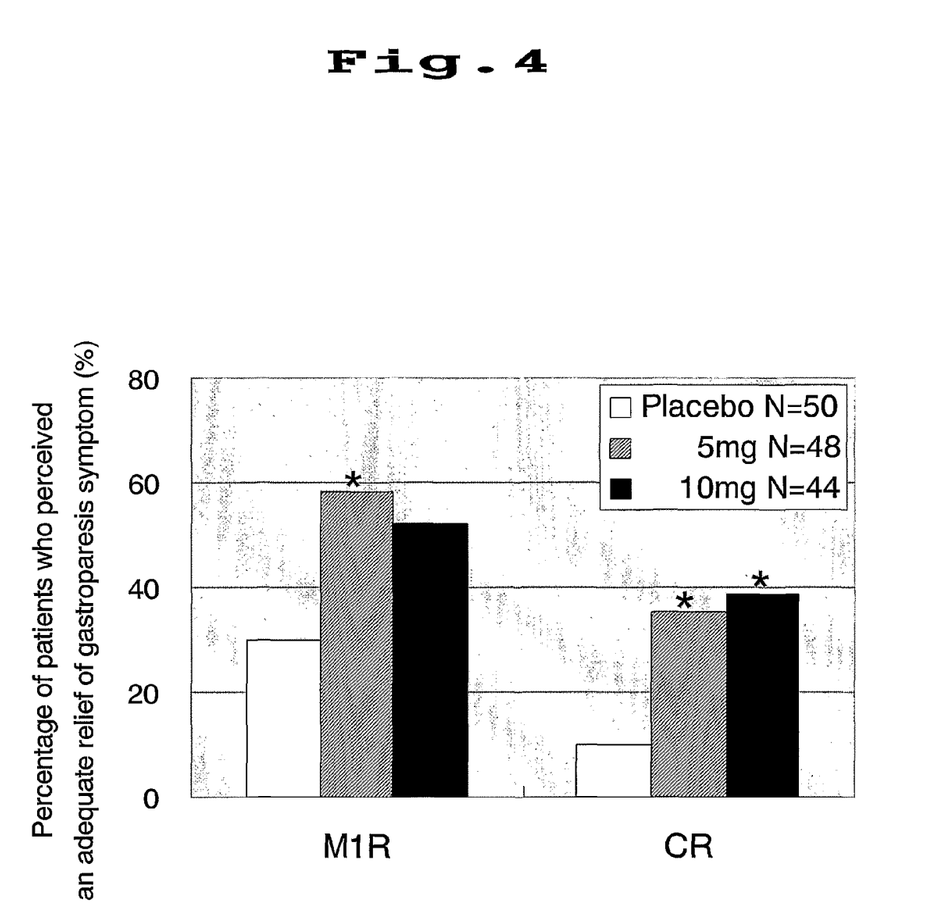
FIG. 4, which is titled "Effect of GM-611 on gastroparesis symptom in diabetic patients of diabetic history longer than 10 years with a normal level of gastric emptying", is a graph showing results of evaluating the percentage of responders who were in the diabetic patients of diabetic history longer than 10 years with the gastroparesis symptom regardless a normal level of gastric emptying and who perceived an adequate relief of gastroparesis symptom by the administration of the therapeutic and/or preventive agent against gastroparesis symptom according to the present invention; M1R (month 1 responder) refers to patients who had adequate relief in at least 50% of weekly evaluations for the first one month of medication and CR (complete responder) refers to patients who were evaluated as monthly responder for three consecutive months.

The results are shown in FIG. 4. Obviously, GM-611 showed a significant efficacy in improving the symptom ($P=0.001$; CR rate in whole GM-611 treated group vs. placebo group by chi-square test). The fact that GM-611 apparently showed a significant improvement in gastroparesis symptom in a dose-dependent manner in the plausibly more homogenous patient groups was considered to show that the compound of the present invention can improve subjective gastroparesis symptom.

In Example 1, GM-611 showed only a tendency to improve the symptom; however, in the analysis using more homogeneous patients (Examples 2, 3 and 4), the compound of the present invention apparently showed significant improvements in subjective gastroparesis symptom, eventually leading to the accomplishment of the present invention.

REFERENCES

The following is a list of references that are relevant to the present invention.

Cucchiara, S., A. Franzese, G. Salvia, L. Alfonsi, V. D. Iula, A. Montisci and F. L. Moreira (1998). "Gastric emptying delay and gastric electrical derangement in IDDM." *Diabetes Care* 21(3): 438-43.

De Block, C. E., I. H. De Leeuw, P. A. Pelckmans, D. Callens, E. Maday and L. F. Van Gaal (2002). "Delayed gastric emptying and gastric autoimmunity in type 1 diabetes." Diabetes Care 25(5): 912-7.

Fang, J., R. McCallum, K. Kipnes, Mark, G. Tougas, B. Miner, Phillip, M. Schmitt, Colleen, L. Abell, Thomas, C. Clinkingbeard, H. Robert, N. Verne and P. Daniel (2001). "GM-611, a motilin-receptor agonist, accelerates gastric emptying in patients with symptomatic gastroparesis (GP)." *Gastroenterology* 120(5): Suppl 1.

Janssens, J., T. L. Peeters, G. Vantrappen, J. Tack, J. L. Urbain, M. De Roo, E. Muls and R. Bouillon (1990). "Improvement of gastric emptying in diabetic gastroparesis by erythromycin. Preliminary studies." *N Engl J Med* 322(15): 1028-31.

Koga, Hiroshi, T. Sato, K. Tsuzuki, H. Onoda, H. Kuboniwa and H. Takanashi (1994). "Potent, acid-stable and orally active macrolide-type motilin receptor agonists, GM-611 and the derivatives." *Bioorganic & Medicinal Chemistry Letters* 4(11): 1347-1352.

Kong, M. F., M. Horowitz, K. L. Jones, J. M. Wishart and P. E. Harding (1999). "Natural history of diabetic gastroparesis." *Diabetes Care* 22(3): 503-7.

Maganti, K., K. Onyemere and M. P. Jones (2003). "Oral erythromycin and symptomatic relief of gastroparesis: a systematic review." *Am J Gastroenterol* 98(2): 259-63.

Russo, A., J. E. Stevens, N. Giles, G. Krause, D. G. O'Donovan, M. Horowitz and K. L. Jones (2004). "Effect of the motilin agonist KC 11458 on gastric emptying in diabetic gastroparesis." *Aliment Pharmacol Ther* 20(3): 333-8.

Talley, N. J. (2003). "Diabetic gastropathy and prokinetics." *Am J Gastroenterol* 98(2): 264-71.

Talley, N. J., M. Verlinden, D. J. Geenen, R. B. Hogan, D. Riff, R. W. McCallum and R. J. Mack (2001). "Effects of a motilin receptor agonist (ABT-229) on upper gastrointestinal symptoms in type 1 diabetes mellitus: a randomised, double blind, placebo controlled trial." *Gut* 49(3): 395-401.

INDUSTRIAL APPLICABILITY

As shown in the above examples, the inventors of the present invention found for the first time that erythromycin derivatives of the formula (1) had an efficacy of improving gastroparesis symptom, which contributed to clinically improving the symptom in patients with symptomatic gastroparesis. This action of the derivatives in improving gastroparesis symptom has not been recognized in ABT-229, an erythromycin derivative conventionally held as an analogous drug, and it was for the first time discovered from the compounds of the present invention. Further, the compounds of the formula (1) according to the present invention are also appropriate for long-term clinical use because of their weaker antibacterial action than that of erythromycin. In view of the foregoing, the present invention provides pharmaceutical agents that are safe and exhibit potent therapeutic and/or preventive effect in the treatment of gastroparesis symptom.

The invention claimed is:

1. A method for treating gastroparesis symptom in a patient with symptomatic gastroparesis, which comprises administering to the patient a therapeutic agent against the gastroparesis symptom which comprises as an active ingredient a compound of formula (1) or a pharmaceutically acceptable salt thereof:

(wherein $R_1$ represents a $C_1$-$C_6$ alkyl group and $R_2$ represents a $C_1$-$C_6$ alkyl group) in a sufficient dose to treat the gastroparesis symptom in the patient, wherein the patient with symptomatic gastroparesis is a patient not involving delayed gastric emptying.

2. The method according to claim 1, wherein $R_1$ is an isopropyl group.

3. The method according to claim 1, wherein $R_2$ is a methyl group.

* * * * *